United States Patent [19]

Bonassa

[11] Patent Number: 5,582,163
[45] Date of Patent: Dec. 10, 1996

[54] RESPIRATORY CONTROL SYSTEM AND APPARATUS

[75] Inventor: Jorge Bonassa, Sao Paulo, Brazil

[73] Assignee: Intermed Equipamento Medico Hospitalar Ltda., Sao Paulo, Brazil

[21] Appl. No.: 166,409

[22] Filed: Dec. 14, 1993

[30] Foreign Application Priority Data

Dec. 6, 1993 [BR] Brazil .................................... 9304638

[51] Int. Cl.$^6$ ................................................. A61M 16/00
[52] U.S. Cl. ............................... 128/204.26; 128/204.21; 128/204.23
[58] Field of Search ........................ 128/204.18, 204.21, 128/204.23, 204.26

[56] References Cited

U.S. PATENT DOCUMENTS

| | | | |
|---|---|---|---|
| 3,669,108 | 6/1972 | Sundblom et al. ................ | 128/204.26 |
| 4,003,377 | 1/1977 | Dahl .................................. | 128/204.23 |
| 4,036,221 | 7/1977 | Hillsman et al. ................ | 128/204.23 |
| 4,448,192 | 5/1984 | Stawitcke et al. ................ | 128/204.26 |

OTHER PUBLICATIONS

"Investigation of the Spontaneous Modes of Breathing of Different Ventilators" by Cox et al.; Intensive Care Med (1988) 14:532–537.

Primary Examiner—Aaron J. Lewis
Attorney, Agent, or Firm—Ladas & Parry

[57] ABSTRACT

A respiratory control system and apparatus for delivering controlled and or assisted respiratory cycles to the patient includes a flow and pressure control valve, exhalation valve, flow transducer, pressure transducer, and a central control unit that servo controls the flow and pressure valve and the exhalation valve based upon the flow and pressure signals from transducers and control panel. The cycles are initiated by detection of inspiratory effort or in accordance to other criteria, maintaining simultaneously the inspired flow and pressure in the airway at or above a predetermined controlled flow and controlled pressure until the delivery of a predetermined controlled volume, and also extending the maintenance of the controlled pressure by a predetermined period of time after the instant in which the volume was completed, and beyond this period until the delivered flow has decreased until a minimum flow threshold level.

17 Claims, 8 Drawing Sheets

RESPIRATORY CONTROL SYSTEM AND APPARATUS

TECHNICAL FIELD

The present invention relates generally to systems for providing supplemental respiratory gas to in vivo respiratory systems, and more particularly for delivering assisted and/or controlled respiratory cycles to the patient. Most particularly, the present invention relates to a respiratory control system and apparatus for delivering assisted and/or controlled cycles to the patient in a manner to improve synchronism between patient effort and gas demand, while assuring predetermined volume delivery at every cycle.

BACKGROUND OF THE INVENTION

The patient submitted to artificial ventilation is connected to a ventilatory system that most often offers the following modalities of ventilation and respective respiratory cycles. The controlled mandatory ventilation (CMV) where the patient receives respiratory cycles named controlled cycles. The controlled cycles are initiated by the machine, and the patient receives a predetermined volume, at also preset flow and respiratory rate. When receiving controlled cycles during CMV the patient is usually sedated and doesn't present any spontaneous inspiratory effort. Consequently the pressure generated in the system depends on the pulmonary mechanics of the patient, that means, airway resistance and pulmonary compliance, and all respiratory work is performed by the respiratory system apparatus, or ventilator. The other modality is termed Continuous Positive Airway Pressure (CPAP), where the patient still intubated and connected to the ventilator is submitted to a pressure termed positive end expiratory pressure (PEEP) and receives respiratory cycles named spontaneous cycle.

The spontaneous cycles are initiated and maintained exclusively by patient inspiratory effort that generates a negative pressure in the airway transmitted to inside the ventilator, that in response delivers proportional flow and volume. Clinical studies showed that the work of breathing associated to spontaneous cycles during CPAP in intubated patients exceed too much the one in normal subjects, because patient has to breath through tubes and pneumatic valves. An alternative to reduce the work of breathing during spontaneous cycles is the modality termed Pressure Support Ventilation (PSV). In this modality, analogous to the spontaneous cycle, the pressure supported spontaneous cycles are initiated by the patient inspiratory effort. When the patient makes the initial inspiratory effort generating a negative pressure, detected by a trigger system, the ventilator increases the pressure in the respiratory circuit until a predetermined level of Pressure Support (PS). Consequently there will be a demand flow proportional to the difference of intrapulmonary pressure and set PS, and inversely proportional to airway resistance. As volume enters the lung, increasing intrapulmonary pressure depending on compliance, diminishes the pressure difference and so on the flow. When the demand flow decreases to a certain level, usually to 25% of maximum flow achieved during the respiratory cycle, the ventilator returns the pressure level to baseline, allowing the patient to exhale. The rationale for this system is to create a pressure gradient increasing the pressure at ventilator side instead of obliging the patient to decrease intrapulmonary pressure by his own effort. Clinical results showed that PSV has decreased successfully the inspiratory workload of intubated patient. However as it occurs during unsupported spontaneous cycle, during pressure supported spontaneous cycle there is no guarantee of delivered volume or number of delivered cycles, what restricts its use in stable patients with reliable inspiratory drive, being more adequate to the weaning phase of ventilation, prior to extubation. Finally, there are two other modalities, the Assisted Controlled Ventilation (A/CV) and Synchronized Intermittent Mandatory Ventilation (SIMV), that present a third type of respiratory cycle, the assisted cycle. The assisted cycle is similar to a controlled one, that delivers a predetermined volume at also preset flow. Different than the controlled cycles, the assisted ones are initiated by patient effort, like the spontaneous cycle. If patient presents inspiratory effort enough to generate a pressure drop equal to the adjusted by assist sensitivity control, the ventilator initiates the flow and volume delivery triggered by his effort. If after triggering the assisted cycle the patient relax, the assisted cycle will perform exactly as a controlled one. However if after onset of assisted cycle the patient maintains the effort, as the flow is maintained constant in the value and pattern adjusted by the operator, the result will be a decrease in the airway pressure. The conventional assisted cycle is unable to respond in terms of flow to patient effort after initiation of the cycle, resulting only in a airway pressure drop and de synchrony between patient effort and gas demand. This occurrence means that the patient is performing a non controlled amount work of breathing throughout the assisted cycle, when ideally the patient should be unloaded in the immediately post controlled ventilation. When becoming to recover gradually his respiratory function the patient would be submitted to a combination of assisted and spontaneous cycles in SIMV, preferably pressure supported, and then moved to a a modality with spontaneous cycles only, like PSV. Clinical studies showed that in many situations the work of breathing associated to assisted cycles exceed those in spontaneous cycle, when theoretically it should be minimum. This has been reported as the cause of respiratory muscles fatigue, obliging patient sedation and extending ventilation time. The ideal assisted cycle should harmonize both guarantee of volume requirements achieved by the controlled cycles, and the synchronization of patient effort and flow demand achieved by pressure supported spontaneous cycles.

DISCLOSURE OF THE INVENTION

It is an object of the present invention to provide a respiratory control system and apparatus for delivering assisted and/or controlled respiratory cycles to the patient, initiated by detection of inspiratory effort or in accordance of a predetermined rate, or to meet other criteria as predetermined minimum minute volume or maximum apnea period, capable of maintaining simultaneously a predetermined minimum controlled flow and a predetermined minimum controlled pressure at the airways until the delivery of a predetermined controlled volume, and also capable of maintaining the predetermined controlled pressure by a predetermined period of time after the instant in which the controlled volume was completed, and also capable of extending this period of time until the delivered flow has decreased until a minimum flow threshold level.

It is further object of this invention to provide a respiratory control system which utilizes a pressure and flow transducers signal output to servo control both flow/pressure and exhalation valves in order to deliver the cycles defined by this invention.

Still further object of this invention is to provide a system of delivering a respiratory cycle generically obtained by combination of spontaneous pressure supported and controlled cycles, termed Volume Assisted and Pressure Supported (VAPS) cycles, more precisely obtained by combining a high impedance flow type source and a low impedance pressure type source, being by this means sensitive to patient spontaneous effort while assuring volume delivery under controlled conditions.

In accordance of this objectives, the respiratory control system and apparatus of the present invention utilizes a control unit responsive to the signal output of pressure and flow transducers to control the flow/pressure and exhalation valves. The control unit receives the signal of controlled volume, controlled flow, controlled pressure, respiratory rate and assist sensitivity threshold from control panel. If patient generates a negative airway pressure, the control unit receives the signal from pressure transducer connected to patient "Y" and compares to the assist sensitivity threshold, initiating a respiratory cycle if the airway pressure reaches the assist threshold. If the airway pressure drop is not enough to reach threshold, the system will initiate a cycle based on the respiratory rate set by operator in the control panel or other initiation criterion. Upon the initiation of the respiratory cycle the system will open the flow/pressure control valve to initially deliver the set controlled flow, monitoring simultaneously delivered flow, volume and airway pressure and closing the exhalation valve at maximum pressure (usually 120 cmH2O). If the resultant measured airway pressure is bellow the value set by operator in the controlled pressure control, the control circuit will continue to open the flow/pressure valve until the airway pressure reaches set value. As result of pulmonary mechanics the control circuit will gradually decrease flow output from flow/pressure valve in order to maintain set controlled pressure level at airway. The control circuit will continuously integrate the flow signal to obtain delivered volume and compare with the operator's predefined controlled volume. While total controlled volume has not been delivered, the inspired flow may decrease until the value of controlled flow set by operator in the control panel. From this point the control system will continue to deliver the set controlled flow until controlled volume is completed. This will increase airway pressure above the minimum value set by controlled pressure control, until the point where the volume is completed. Depending on settings and pulmonary mechanics, the volume may be delivered while the flow is above set controlled one, and then airway pressure will be maintained at set controlled pressure level. The operator may set a inspiratory hold time, that will be the period of time when the control circuit will maintain the set pressure control level after tidal volume has been completed, Thus, if exists a pressure gradient between inside of the lung and the airway, the control circuit will continue to deliver flow, and consequently volume, in proportion to this pressure difference and pulmonary mechanics. In the hold time period the constraint of minimum controlled flow is deactivated, and the delivered flow may decrease bellow this value, until zero if the hold time is long enough. Also the pressure reference for servo control of exhalation valve in this period is switched from maximum pressure to the controlled pressure level. That means that if airway pressure increases above controlled pressure level, the exhalation valve will open to let gas escape and airway pressure decrease to set level. In addition the control circuit may, by option of operator, extend the cycle duration until the inspired flow decrease to a minimum threshold level, usually 25% of the maximum flow obtained during the cycle. The control unit of the present invention further includes a alarm control that limits the maximum pressure in the cycle, initiating exhalation once reached. Other objects, advantages and aspects of the invention will become apparent upon reading of following detailed description and claims and upon reference to the accompanying drawings.

DETAILED DESCRIPTION OF THE INVENTION

Figure 1:
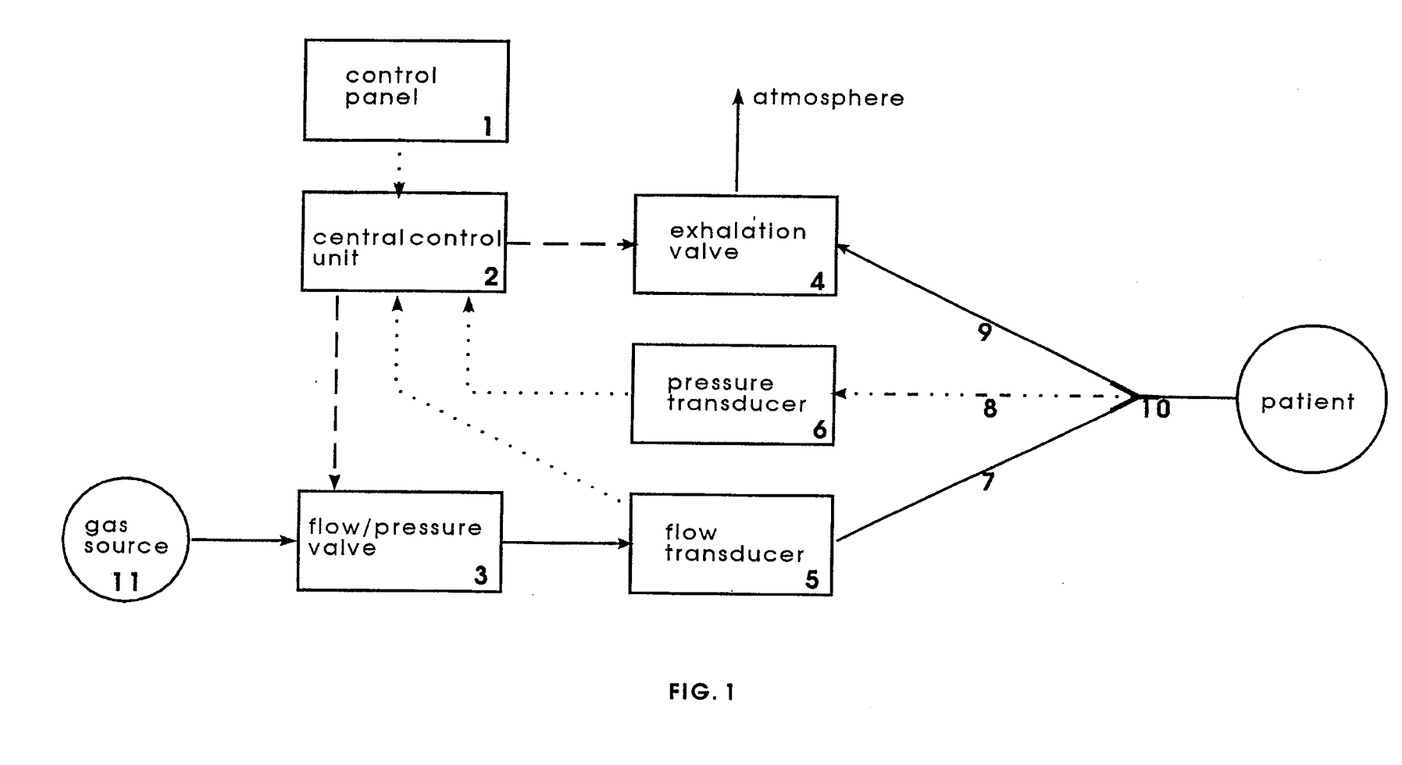
FIG. 1 is a block diagram of respiratory control system embodying the present invention.
Figure 2:
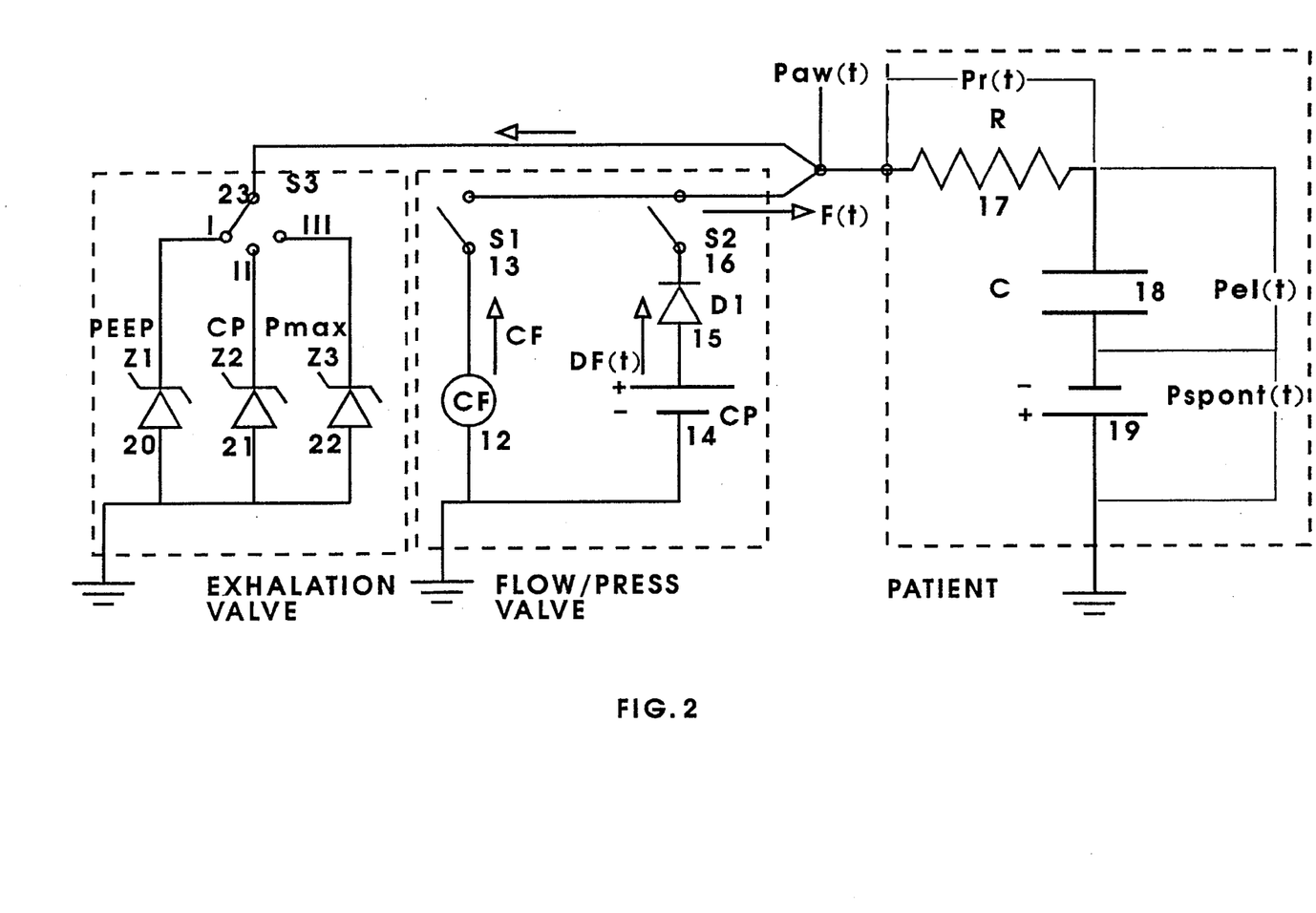
FIG. 2 is a graph showing schematic representation of respiratory control system and patient through analog electric circuit.

FIG. 1 is a simplified illustration of the respiratory control system. It includes a flow/pressure control valve 3 connected to the conditioned gas supply source 11, that controls flow delivery to the patient through a inspiratory tube 7 connected to the "Y" type connector 10. From patient the gas is exhaled through the expiratory tube 9 by the control of exhalation valve 4. Airway Pressure is transmitted from "Y" connector 10 to the pressure transducer 6 through the tube 8, and inspiratory flow is sensed by the flow transducer 5 after flow/pressure control valve, Both signals of flow and pressure of transducers, plus the input from control panel 1, are used by the central control unit to servo actuate the flow/pressure and exhalation valves. Valve units 3 and 4 are preferably microprocessor servo actuated, however may be activated by solenoids and/or by pneumatic pilot control signals, under the main control of the central control unit. The central control unit 2 also is preferably to employ microprocessor, however may use conventional digital and analog circuits. Flow sensor is preferably a transducer independent of flow/pressure valve, however may be incorporated inside the valve indicating a signal proportional to valve opening, that indirectly will be related to flow, In FIG. 2 is showed a model based on electrical circuit analogy that represents the respiratory control system and patient respiratory system in its essential. The patient respiratory system is represented by a resistance R 17, analogous to airway resistance, a capacitor C 18, analogous to pulmonary compliance, a voltage source Pspont(t) 19, analogous to patient effort. The flow and pressure valve of respiratory control system is represented by a current source, analogous to flow source (CF) 12 connected in parallel with a voltage source, analogous to pressure source (CP) 14. The voltage source is connected by a unidirectional element, a diode 15, that prevents current (flow) being drained through voltage (pressure) source if the voltage (pressure) in the system happens to be higher than the voltage (pressure) regulated by this source. Both CF and CP sources are connected to the patient respiratory system through switches S1 13 and S2 16. The exhalation valve is represented by three zener diodes Z1 20, Z2 21 and Z3 22 connected to the system by a three position switch S3 23, that allows the selection of each one depending upon the respiratory cycle phase. Each zener diode are capable of draining current (flow) until the voltage (pressure) in the system drop to its voltage (pressure) reference. The references of each zener Z1, Z2 and Z3 in positions I, II and III are respectively ambient or PEEP pressure, controlled pressure CP level and maximum pressure Pmax level. After analogous system description the pneumatic terminology will be used instead electrical, however always based on the model. From the model it's obtained the motion equation for respiratory system.

$$Paw(t)=F(t)\times R+V(T)/C-Pspon(t) \quad (I)$$

and $$Pr(t)=F(t)\times R$$

$$Pel(t)=V(t)/C$$

where

F(t) is the instantaneous total inspiratory flow delivered to the patient, result of flow and pressure sources output, in Liters per seconds (LPS);

R is the resistance of respiratory system airways, in cmH2O per liters per seconds (cmH2O/LPS);

V(t) is the instantaneous delivered volume, obtained by the integration of F(t) in the interval of time between cycle initiation t0 and the considered time t, in liters (L);

C is the compliance of respiratory system, in cmH2O per liter per sec.

Pel(t) is the elastic pressure generated by the delivered volume V(t) in function of C, in cmH2O.

Pr(t) is the resistive pressure generated by the delivered flow F(t) in function of R, in cmH2O.

Pspont(t) is the instantaneous pressure generated by the actuation of patient respiratory muscles, in cmH2O.

At any instant, the flow output from control system to patient system is given by:

$$F(t)=(Paw(t)-Pel(t)+Pspont(t))/R \quad (II)$$

If both CF 12 and CP 14 sources are connected to the patient the total flow output will be the summation of the flow of each source. The CF flow source 12 is a high impedance source, capable of maintaining a predetermined controlled flow CF independent of system pressure. On the other hand the CP source 14 is a low impedance flow source, delivering a demand flow DF(t) in dependence of the controlled pressure CP level and the system pressure. The total flow delivered to the system will be:

$$F(t)=CF+DF(t) \quad (III)$$

The flow output of controlled pressure CP source 14 DF(T) is pressure dependent and can be obtained from equations (II) and (III) maintaining Paw(t) equal to controlled pressure CP in equation and applying equation (III).

$$DF(t)=(CP-Pel(t)+Pspont(t))/R-CF \quad (IV)$$

Due to the presence of the unidirectional element 15 in the flow/pressure valve model, DF(t) can't assume negative values, consequently some conditions must be added to equation (III):

F(t)=CF+DF(t), if DF(t) obtained in equation (IV) is higher than zero, or

F(t)=CF, if DF(t) obtained in equation (IV) is lower or equal zero.

It means that Paw(t) is maintained at least at CP level, however it can increase above this value by the action of the controlled flow CF, while the two CP and CF sources are connected.

From equation (IV) its evident the dependence of demand flow DF(t) and patient effort Pspont(t), Pel(t), Pr(t) and Paw(t). Consequently the pressure source 14 represents a variable flow source, sensitive to patient effort and respiratory system mechanics (R and C). As result of this combination there is a total flow output F(t) incorporating a component capable of assuring flow and volume delivery independent of pressure, and other capable of augmenting flow as function of patient demand.

If only CP source 14 is connected to the patient then F(t), without the controlled flow CF component, will be equal to the demand flow DF(t) obtained by equation (III), and the system pressure Paw(t) equal to CP.

If only CF source 12 is connected then F(t), without demand flow DF(t) component, will be equal to the controlled flow CF, and the system pressure Paw(t) obtained by equation (I).

Figure 3:
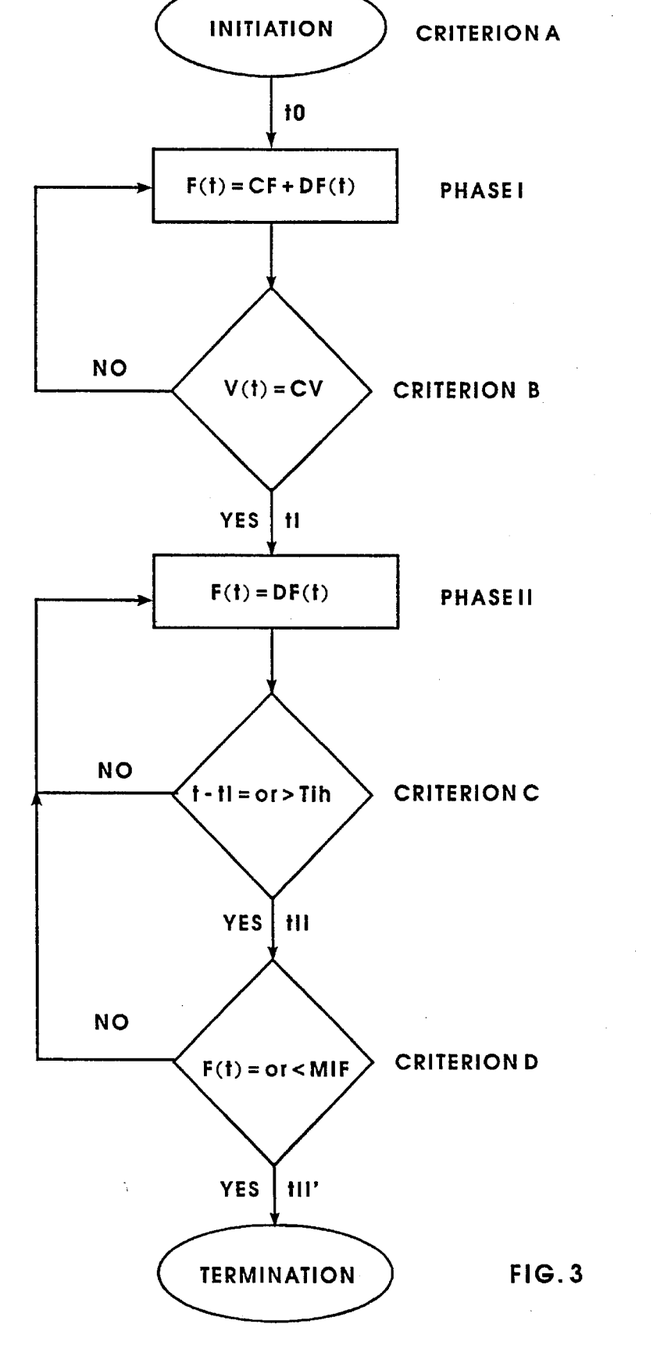
FIG. 3 is a flow chart illustrating system control for VAPS assisted-controlled cycle.
Figure 4A:
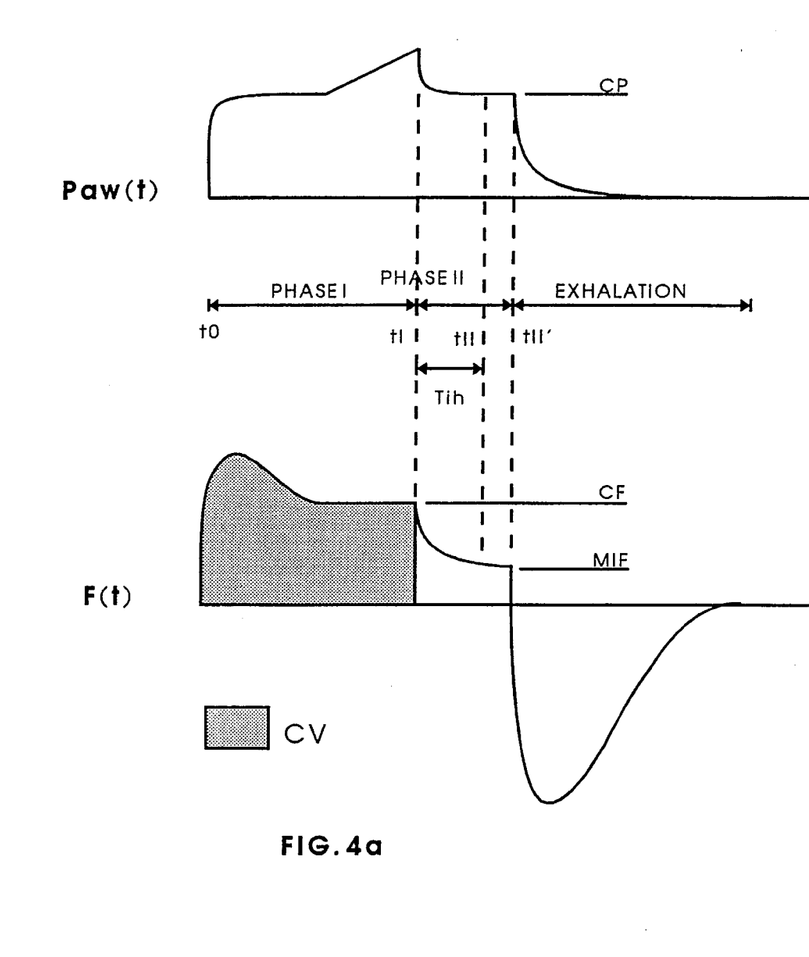
FIG. 4a, 4b, 4c, 4d, 4e, 4f and 4g are graphical illustrations showing pressure and flow tracings of VAPS cycles provided by the respiratory control system.

The respiratory VAPS cycle delivered by the system above presented through its mathematical model, is defined by the following events and phases, illustrated by the flow chart of FIG. 3 and the pressure and flow tracings of FIG. 4a:

i. Initiation: The cycle is initiated, at instant t0, based upon the detection of patient effort by suitable means, or to meet requirements of predetermined respiratory rate, or minimum minute volume, or maximum apnea period, or other criterion, generically initiation criterion A.

ii. Phase I: The Phase I is obtained by connecting both flow and pressure sources 12 and 14, (switches S1 13 and S2 16 closed) and closing exhalation valve at Pmax (S3 23 at position III).

iii. Termination of Phase I and initiation of Phase II: Phase I is terminated at instant t1 whenever the termination criterion B is verified. Termination criterion B is based on Volume, and is verified whenever delivered volume V(t) reaches predetermined controlled volume CV. The termination of Phase I initiates Phase II.

iv. Phase II: The Phase II, subsequent to Phase I termination, is obtained by disconnecting the controlled flow CF source 12 (switch S1 13 open), while maintaining CP source 14 connected (switch S2 16 closed). The exhalation valve pressure threshold is also changed to the CP level (switch S3 23 at position II).

v. termination of Phase II (conclusion of VAPS cycle): Phase II is terminated at time t11 when termination criteria C is verified, or at instant t11' when criterion D is verified, what occurs last. Criterion C is based on time, and is verified at instant t11 whenever the period of time measured since Phase I termination, at instant t1, reaches the value of a predetermined period of time Tih (inspiratory hold time), that is (t - t1) equal or higher than Tih. Criterion D is base on flow, and is verified at instant t11' whenever the delivered flow DF(t) reaches a certain minimum flow level MIF, that is, DF(t) equal or lower than MIF. This MIF level may be predetermined by operator, or automatically adjusted based on the maximum delivered flow MAF obtained throughout the cycle.

Any one of criterion B, C and D may be disabled by user's option, resuming respective phase according.

In FIG. 4a all phases and representative instants of the VAPS cycle are presented. The shaded area represents the controlled volume CV. In this example, in the middle of the cycle the flow F(t) decrease to controlled flow CF level, and the pressure Paw(t) was increased over controlled pressure CP to assure controlled volume CV delivery. After the volume was completed at instant tl, the pressure Paw(t) decreased to controlled pressure CP level during inspiratory hold time Tih period. At instant tll, when the Tih period was terminated the flow F(t) was above the minimum flow MIF level, consequently the end of the cycle was retarded until instant tll' when the minimum flow MIF threshold level was reached.

Figure 4B:
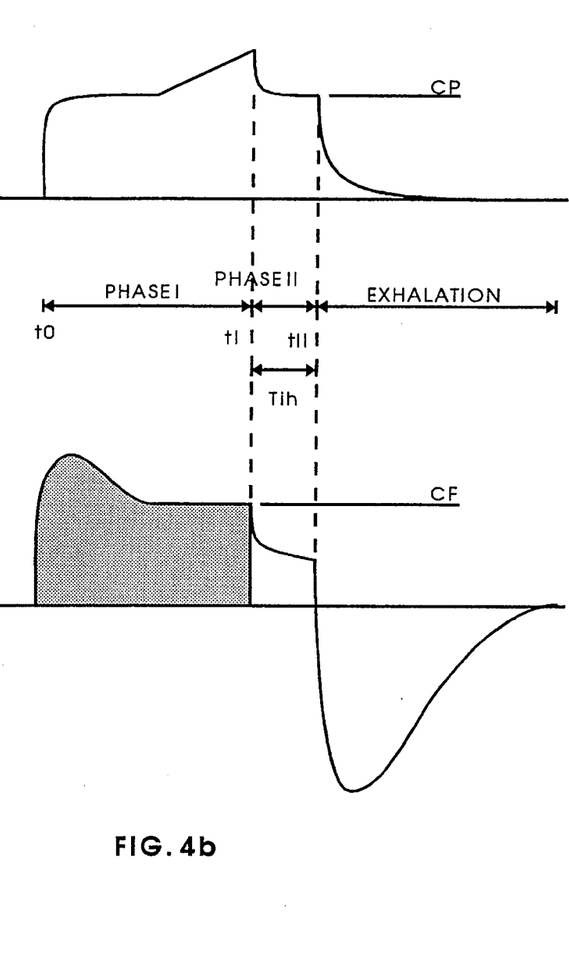

In FIG. 4b is showed the previous example with criterion D of minimum flow MIF disabled and the cycle terminating just after the inspiratory time Tih period, at instant tll. The total volume delivered in this case is lower than the previous example.

Figure 4C:
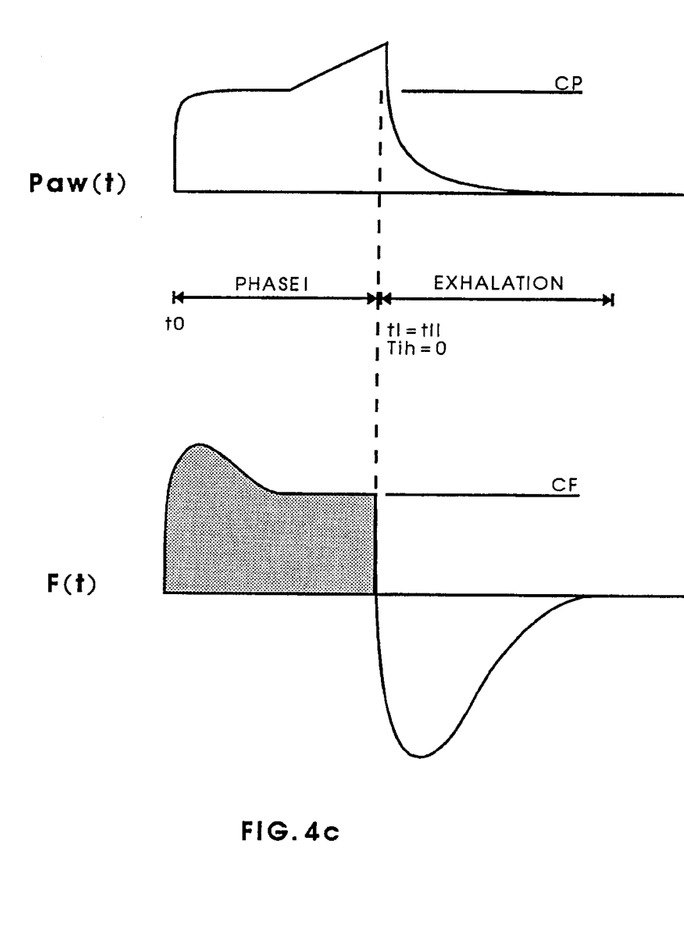

In FIG. 4c also criterion C was disabled, that is, the inspiratory hold time Tih was set at zero, and the cycle terminating at instant tl, when the controlled volume CV was completed. Again, the total volume delivered in this case is lower than in previous example.

Figure 4D:
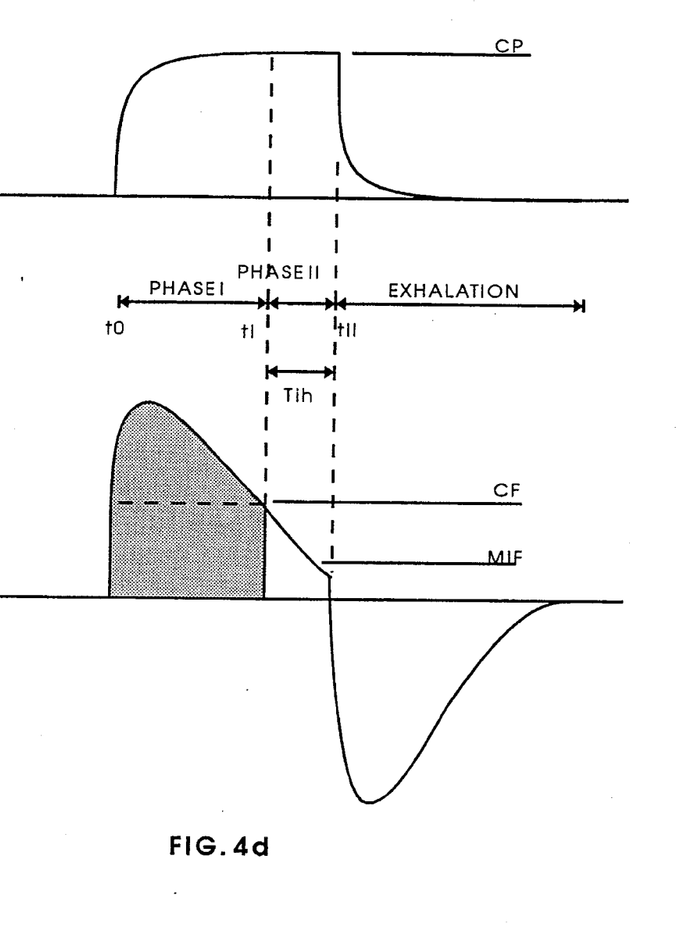

In FIG. 4d, like the example of FIG. 4a, both criterion are enabled, however how the controlled pressure CP level was set higher than in previous examples, the controlled volume CV was delivered while the flow F(t) was above the controlled flow CF level, and pressure was maintained at controlled pressure CP level. Also the flow F(t) decreased below the minimum flow MIF level during the period of inspiratory hold time Tih, consequently criterion D was verified before criterion C, and the cycle terminated at instant tll.

Figure 4E:
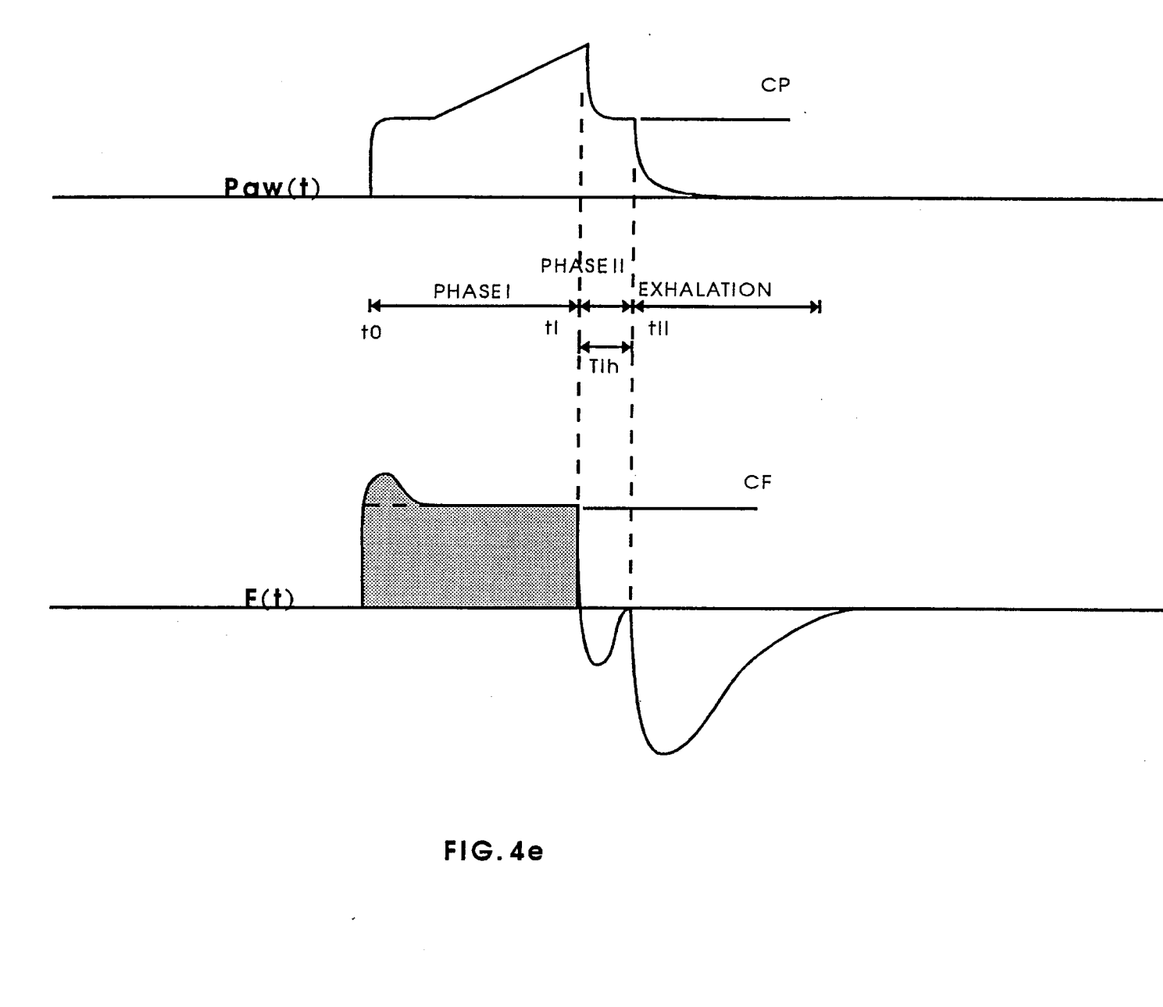

In FIG. 4e, contrary to the last example, a lower controlled pressure CP was used. Consequently to decrease the pressure Paw(t) to the controlled pressure level during controlled inspiratory hold Tih period, it was necessary to exhale partially the admitted controlled volume CV.

Figure 4F:
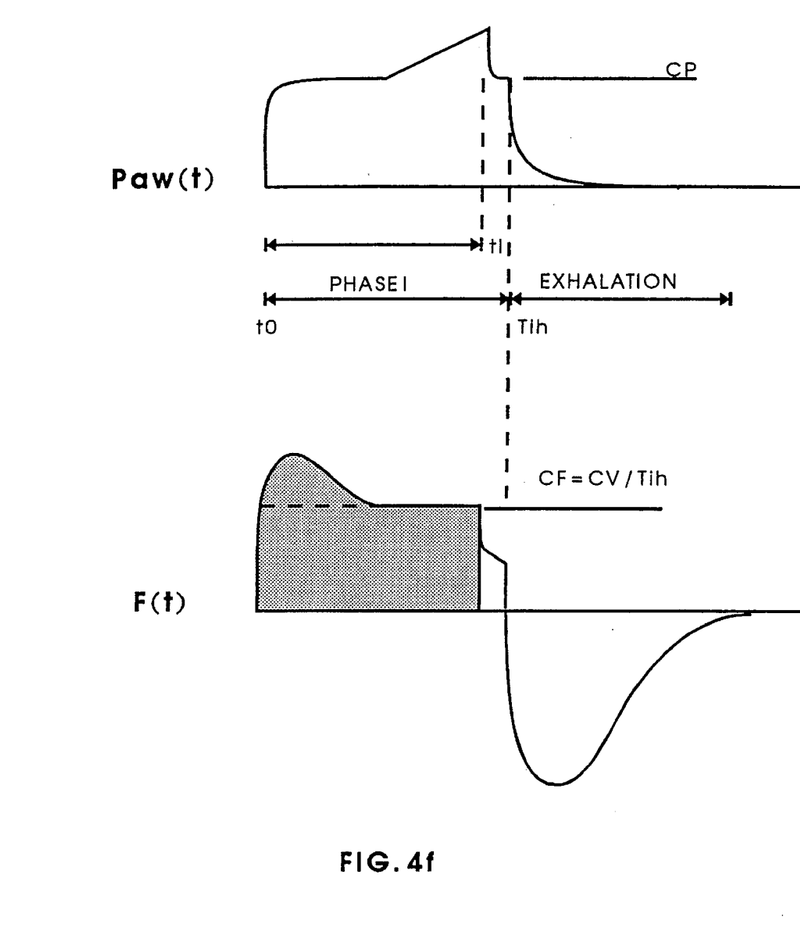

A variation of VAPS cycles described above and showed in FIG. 4f, is obtained by computing the period of controlled inspiratory hold time Tih since the beginning of the cycle, at instant tO, and not since the instant tl when the controlled volume CV has been completed, and also adjusting the controlled flow CF indirectly, based on the controlled volume CV and controlled inspiratory time Tih, according the following relation:

$$CF=CV/Tih$$

Figure 4G:
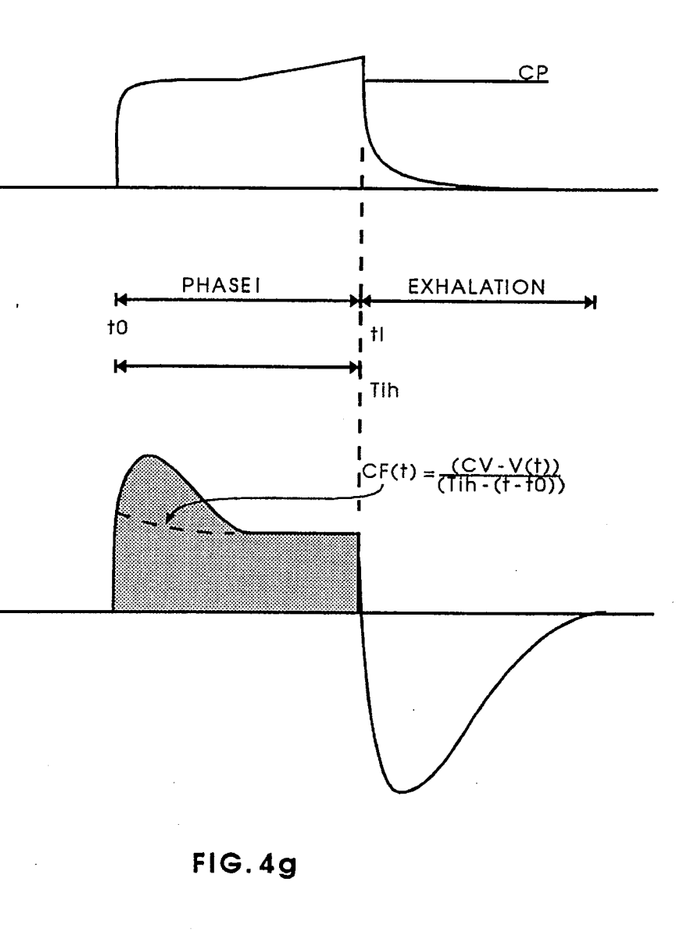

Another variation showed in FIG. 4g is obtained similarly computing the period of controlled time Tih since the beginning of the cycle, at instant tO, and obtaining the controlled flow as a function of time CF(t), based on controlled volume CV and controlled inspiratory time Tih, according the following relation:

$$CF(t)=(CV-V(t))/(Tih-(t-tO))$$

that means, at every instant, it is verified the mean flow CF(t) necessary to complete the rest of volume (CV−V(t)) to complete the controlled volume CV, in the rest of time (Tih−(t−tO) to complete the period of controlled inspiratory time Tih.

vi. Expiratory phase: The expiratory phase subsequent to Phase II, terminated at tll or tll', what occurs last, is obtained by closing previous connected sources (switches S1 13 and S2 16 open) and opening exhalation valve at atmospheric or PEEP pressure level (switch S3 23 in position I).

Figure 5:
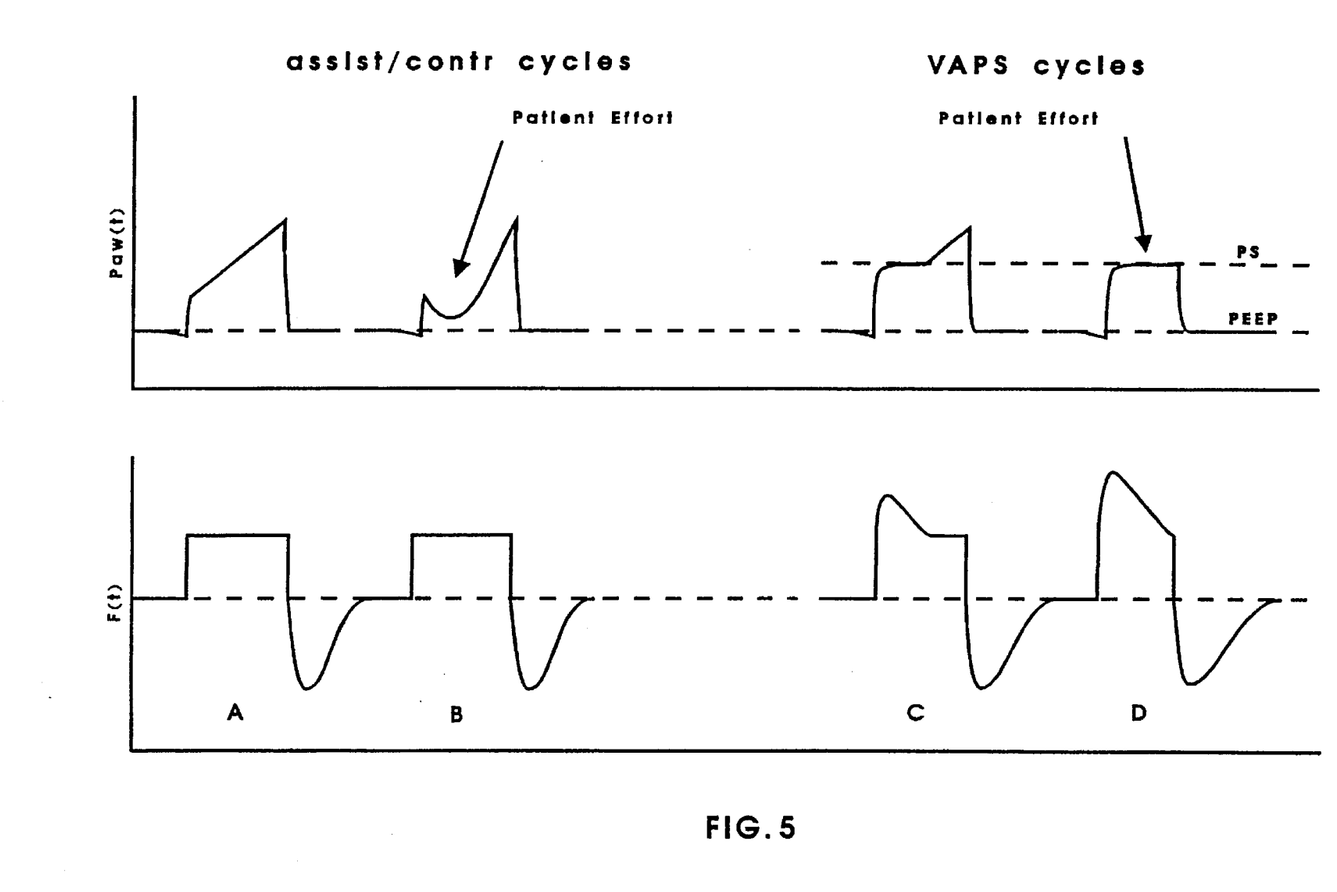
FIG. 5 shows graphical illustrations showing pressure and flow tracings of conventional assisted cycles and VAPS cycles.

FIG. 5 shows the pressure and flow tracings for conventional assisted cycles and VAPS cycles in the same conditions.

In the first example of conventional assisted cycle shown in FIG. 5, cycle A, the patient made a effort enough to initiate cycle and relaxed. The flow delivered F(t) is a predefined square wave CF, obtained by a flow source similar to the source 12 of the model of FIG. 2, This flow is maintained until the set controlled volume CV is completed. The Paw(t) increases according motion equation (I) incorporating the two components Pr(t) and Pel(t), In the next example of conventional assisted cycle shown in FIG. 5, cycle B, the patient maintain effort throughout the cycle. The Paw(t) incorporates now the Pspont(t) term that is subtracted from (Pel(t)+Pr(t)). Consequently Paw(t) decreases compared to the Paw(t) in cycle A of FIG. 5. The important characteristic of this cycle is that flow is not modified in spite of patient effort, because flow is delivered by a high impedance flow source type only, insensitive to system pressure. The difference between the area bellow Paw(t) in relaxed and active patient relates to the work of breathing performed by the active patient.

FIG. 5, cycle c, shows the pressure and flow tracings for VAPS cycle, when the patient made a inspiratory effort initiating the cycle and then relaxed. In this case, as the pressure Paw(t) obtained only by the effect of controlled flow CF resulted below the level of controlled pressure CP, the F(t) is increased over CF by a demand flow DF(t) until Paw(t) reaches CP. F(t) decreases as volume is delivered and Pel(t)increases, reaching in the example, the CF level before CV is completed. From this point Paw(t) increases over CP until CV is achieved. Compared with cycle A, in cycle C the mean flow was higher and consequently inspiratory time decreased for the same volume CV. For the patient that maintains inspiratory effort even after triggering cycle, showed in cycle D of FIG. 5, as F(t)is servo controlled to maintain Paw(t) at least at CP level, F(t) is augmented by DF(t) in proportion to the difference between CP and (Pel(t)−Pspont(t)). Consequently F(t) is sensible to patient effort, eliminating Paw(t) deflection and decreasing patient work of breathing.

The present invention is not limited to the exemplary respiratory control system apparatus shown embodying that invention. Modifications may be made by the use of alternative and or foregoing technologies. It is, therefore, contemplated by the append claims to cover the essential features of this invention or encompasses the true spirit and scope of the invention.

I claim:

1. A method for delivering a controlled volume of breathable gas to a patient to improve synchronism between patient effort and system flow demand while assuring desired minimum requirements for airway pressure, flowrate and volume, the method comprising:

providing a respiratory circuit including an inspiratory tube, expiratory tube, exhalation valve and flow/pressure valve;

monitoring airway pressure at airway entry of a patient;

initiating breathable gas volume delivery to a patient's airway at the trigger instant upon detection of an inhalation attempt by a patient which is sufficient to lower airway pressure to a reference trigger pressure;

at trigger instant, opening the flow pressure valve to deliver desired controlled flowrate through said inspiratory tube of said respiratory circuit, at the same time closing the end of the expiratory tube of the respiratory circuit using the exhalation valve and maintaining the respiratory circuit closed during inhalation up to a maximum acceptable airway pressure;

beginning to monitor at trigger instant, the flowrate and delivered volume of breathable gas during inhalation by a patient, said step of monitoring continuing throughout a respiratory cycle;

continuing to deliver breathable gas to patient by the flow/pressure valve, comparing actual airway pressure monitored at airway entry of the patient with the desired controlled pressure;

if patient monitored airway is below desired controlled pressure, continuing to deliver breathable gas to patient, increasing flowrate at airways above desired controlled flowrate, based upon the difference of monitored air pressure and desired controlled pressure, to null existing pressure differences, said step of delivering continuing throughout inspiratory portion of the respiratory cycle, until delivered volume reaches desired controlled volume;

if patient monitored airway pressure is above desired controlled pressure, continuing to deliver breathable gas to the patient, maintaining desired controlled flowrate at airways, said step of delivering continuing throughout inspiratory portion of the respiratory cycle, until delivered volume reaches desired controlled volume; and at the volume completion instant in which the delivered volume reaches desired controlled volume, terminating the delivery of the controlled volume of breathable gas to patient by closing flow/pressure valve thus decreasing the flowrate through said inspiratory tube of said respiratory circuit to zero, opening the exhalation valve so as to permit such a patient to exhale the delivered volume and thus decreasing airway pressure to a predetermined positive and expiratory pressure.

2. A method as claimed in claim 1 further comprising:

extending inhalation beyond volume completion instant by a desired inspiratory hold time, maintaining inspiratory phase of respiratory cycle until desired inspiratory hold time elapses;

during said inspiratory hold time period, if patient monitored airway pressure is below desired controlled pressure, continuing to deliver breathable gas to the patient, controlling flowrate at airways based solely upon the difference of monitored air pressure and desired controlled pressure, to null existing pressure difference, said step of delivering continuing throughout inspiratory hold time portion of the respiratory cycle, until inspiratory hold time has elapsed;

during said inspiratory hold time period, if patient monitored airway pressure is above desired controlled pressure, opening in a controlled manner the exhalation valve based upon the difference between the desired controlled pressure and monitored airway pressure, to null existing pressure differences, said step of delivering continuing throughout inspiratory hold time portion of the respiratory cycle, until inspiratory hold time elapses; and at the instant in which inspiratory hold time elapses, terminating the delivery of the controlled volume of breathable gas to patient by closing flow/pressure valve thus decreasing the flowrate through said inspiratory tube of said respiratory circuit to zero, opening the exhalation valve so as to permit such a patient to exhale the delivered volume and thus decreasing airway pressure to a predetermined positive and expiratory pressure.

3. A method as claimed in claim 1 further comprising:

extending inhalation beyond the volume completion instant by an additional flow supplementation period, maintaining inspiratory phase of respiratory cycle until the flowrate through said inspiratory tube of said respiratory circuit decreases to a predetermined minimum flowrate threshold;

during said additional flow supplementation period, if patient monitored airway pressure is below desired controlled pressure, continuing to deliver breathable gas to the patient, controlling flowrate at airways based solely upon the difference of monitored air pressure and desired controlled pressure, to null existing pressure difference, said step of delivering continuing throughout additional period, until the flowrate decreases to a predetermined minimum flowrate threshold; and at the instant in which flowrate decreases to predetermined minimum flowrate threshold, terminating the delivery of the controlled volume of breathable gas to patient by closing flow/pressure valve thus decreasing the flowrate through said inspiratory tube of said respiratory circuit to zero, opening the exhalation valve so as to permit such a patient to exhale the delivered volume and thus decreasing airway pressure to a predetermined positive and expiratory pressure.

4. A method as claimed in claim 3 in which the value of minimum flowrate threshold that terminates the breathable gas volume delivery to a patient is determined as a percentage of the maximum flowrate monitored during the initiation of inhalation.

5. A method as claimed in claim 1, in which the desired controlled flowrate is a predetermined constant value.

6. A method as claimed in claim 1 in which the desired controlled pressure is a predetermined constant value.

7. A method as claimed in claim 1 in which the desired controlled flowrate is the ratio of desired controlled volume and a desired inspiratory time.

8. A method as claimed in claim 1 in which the desired controlled flowrate is determined during first steps of inhalation based upon a predetermined equation until the difference between monitored airway pressure and desired controlled pressure diminishes to a predetermined value.

9. A method as claimed in claim 1 in which the desired controlled flowrate is a time dependent mathematical function, representing predetermined waveform.

10. A method as claimed in claim 1 in which the desired control flowrate is determined based upon the difference between monitored airway pressure and desired controlled pressure and the rate of change of monitored airway pressure between predetermined time period steps.

11. A method as claimed in claim 1 in which the desired controlled flowrate is determined and continuously updated at predetermined time steps since the initiation of inhalation, computing at every instant the remainder of the volume to complete desired controlled volume (desired controlled volume subtracted from delivered volume at given instant) and the remainder of the inspiratory time (desired controlled inspiratory time subtracted from period of time since initiation of inhalation), and obtaining the instantaneous desired controlled flowrate by the ratio of the remainder of the volume and the remainder of the inspiratory time.

12. A method as claimed in claim 1 in which the desired controlled pressure is determined and continuously updated after a predetermined number of respiratory cycles, as a direct proportion of the average mean delivered flowrate.

13. A method as claimed in claim 1 in which the desired controlled pressure is determined and continuously updated after a predetermined number of respiratory cycles, based upon the patient's respiratory system impedance, determined by any means.

14. A method as claimed in claim 1 in which the predetermined positive end expiratory pressure reached during exhalation is zero.

15. A method as claimed in claim 1 in which the breathable gas volume delivery is automatically initiated based upon a desired respiratory rate.

16. A method as claimed in claim 1 in which the breathable gas volume delivery is automatically initiated upon the detection of the occurrence of a patient's apnea period which is longer than a desired maximum allowable apnea interval.

17. A method as claimed in claim 1 in which the breathable gas volume delivery is automatically initiated upon the detection of the occurrence of a decrease on monitored minute volume, comprising the summation of the volume delivered in every inhalation during the last minute, which is lower than a desire minimum allowable minute volume.

\* \* \* \* \*